United States Patent [19]

Krotkiewski

[11] Patent Number: 5,141,927
[45] Date of Patent: Aug. 25, 1992

[54] ANTIHYPERTENSIVE PREPARATION COMPRISING AN ALGINATE AND VITAMIN D

[76] Inventor: Marcin Krotkiewski, S-436 00, Askim, Sweden

[21] Appl. No.: 558,777

[22] Filed: Jul. 26, 1990

[51] Int. Cl.$^5$ ............ A61K 31/07; A61K 31/715
[52] U.S. Cl. .................. 514/54; 514/167; 514/884; 536/3
[58] Field of Search ............ 536/3; 514/167, 54, 514/884

[56] References Cited

U.S. PATENT DOCUMENTS

| | | | |
|---|---|---|---|
| 4,780,534 | 10/1988 | Lebbar et al. | 536/3 |
| 4,789,664 | 12/1988 | Seligson et al. | 514/23 |
| 4,797,300 | 1/1989 | Jandacek et al. | 536/119 |
| 4,840,894 | 6/1989 | Schachter et al. | 435/7.25 |
| 4,859,688 | 8/1989 | Yamaguchi et al. | 514/824 |
| 4,871,723 | 10/1989 | Makino et al. | 514/167 |
| 4,897,387 | 1/1990 | Ikekawa et al. | 514/167 |
| 4,897,388 | 1/1990 | Malluche | 514/167 |
| 4,962,092 | 10/1990 | Wood | 514/23 |
| 4,983,268 | 1/1991 | Kirkpatrick et al. | 536/3 |
| 5,030,626 | 7/1991 | Hamma et al. | 514/167 |

FOREIGN PATENT DOCUMENTS

| | | |
|---|---|---|
| 0227553 | 7/1987 | European Pat. Off. . |
| 1070910 | 12/1959 | Fed. Rep. of Germany . |
| 60-206801 | 10/1985 | Japan . |
| 589956 | 1/1978 | U.S.S.R. . |
| 760030 | 10/1956 | United Kingdom . |

*Primary Examiner*—Ronald W. Griffin
*Attorney, Agent, or Firm*—Ostrolenk, Faber, Gerb & Soffen

[57] ABSTRACT

Alginates capable of binding sodium and having ion exchanging capacity are used in conjunction with vitamin D for the treatment of hypertension. Such alginates may be acid extracted from seaweeds such as Asophylum nodosum. The acid-extracted alginate may be converted, for example, to potassium alginate prior to administration or mixing with vitamin D to form pharmaceutical compositions.

11 Claims, 5 Drawing Sheets

TESTPERIODS

***p<0.001 vs period R
**p<0.01 vs period R
*p<0.05 vs period R

TESTPERIODS
***p<0.001 vs period R
** p<0.01 vs period R

TESTPERIODS
***p<0.001
*p<0.05

ANTIHYPERTENSIVE PREPARATION COMPRISING AN ALGINATE AND VITAMIN D

BACKGROUND OF THE INVENTION

Mild hypertension, i.e. a diastolic blood pressure between 90–104 mm Hg, emerges as a very common condition in the adult population of the affluent societies. Seventy per cent of the hypertensive population can be classified as belonging to this group. The condition of mild hypertension is considered by most groups to be associated with a higher risk of cardiovascular complications and to deserve active therapeutical intervention. As the pharmacological treatment is reported to be associated with the development of hyperlipemia and hyperglycemia, all efforts to find non-pharmacological means for the treatment of these conditions deserve close attention and critical clinical assessment of their availability.

The decrease in body weight, the lowering of sodium intake and high intake of dietary fibers have been proved to ameliorate increased blood pressure. In cases of weight reduction and the application of dietary fibers, the degree of blood pressure lowering has been comparable to that induced by pharmacological treatment with beta-blockers.

The available clinical experience suggests that the compliance with the diet required for the maintenance of the treatment effects is rather poor. The possible blood pressure-lowering effect of an increased intake of polyunsaturated fatty acids, high potassium, and magnesium despite overmentioned encouraging reports, still requires better verification.

SUMMARY OF THE INVENTION

The object of the present invention is to find a natural product that is easy to apply and sufficiently palatable to avoid relying exclusively on the patient's motivation for its administration, as in the case of different diets, but which is nevertheless effective in ameliorating mild hypertension.

This has according to the invention been achieved by a preparation containing a dietary polymeric substance, e.g. a polysaccharide or the like, and vitamin D or derivatives/analogues thereof.

BRIEF DESCRIPTION OF THE DRAWINGS

The invention will below be described in more detail with reference to the accompanying drawings, which in the form of diagrams show the result of clinical studies performed with the preparation according to the invention.

BRIEF DESCRIPTION OF THE PREPARATION

Figure 1:
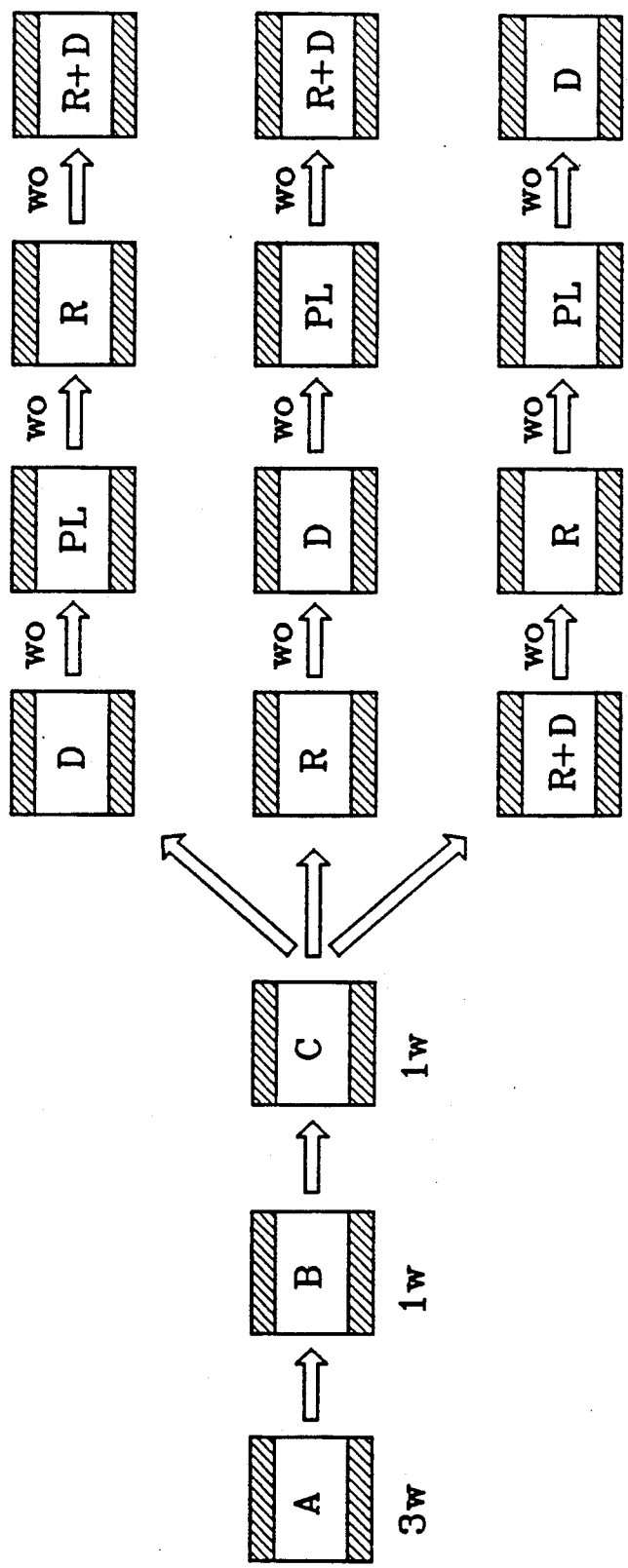
FIG. 1 illustrates the design of a comparative study with the preparation according to the present invention.

Asophylum nodosum is a seaweed plant, one of the algae, that grows in the waters along the Scandinavian west coast bordering the North Sea. In vitro studies showed that these brown algae are to be treated as ion exchangers as they were found to adsorb sodium and release potassium to the liquid medium.

Preliminary in vivo experiments, especially in spontaneously hypertensive rats (SHR), showed a clear blood pressurelowering effect of the seaweed preparation. Similar algae are used as a popular appetizer (Wakama) by Japanese people in coastral areas where fewer hypertensive patients are found. Clinical studies by the inventor of the present invention on patients with mild hypertension, showed a clear blood pressure-lowering effect of the seaweed preparation.

Asophylum nodosum was used when preparing the seaweed preparation of the present invention. The seaweed was milled and washed with acid (e.g. HCl) and water. Water and alkali was added to extract alginate. The extract was clarified and filtered. A metal salt, such as a calcium or magnesium salt, e.g. calcium chloride, was added to precipitate alginate and the precipitate was washed with water and acid to obtain alginic acid. The algininc acid was neutralized with an alkaline potassium compound, e.g. potassium carbonate, and the potassium alginate thus obtained was dried and milled.

It is of course also possible to use other algae preferably brown algae, containing alginate. Alginates in pure form may also be used.

Alginates are polysaccharides and it would also be possible to use other types of polysaccharides with sodium-binding (ion-exchanging) capacity, e.g. pectin, xanthan, galactomannans, glucomannans etc. Other esculent polymeric substances with similar properties may also be used. The polymeric substance may be used either in pure form or contained in dietary fibers of different kind.

The vitamin D used in the preparation was a vitamin D derivative (1.25-dihydroxycholecalcipherol with the trade name (Calcitriol (R)) and the amount thereof was 0.02 $\mu$g per capsule containing 0.5 g potassium alginate. An appropriate daily dose in about 5 g. The ratio between vitamin D and potassium alginate may of course be varied within certain limits. The vitamin D can also be present in natural form, e.g. cod liver oil. Other derivatives or analogues of vitamin D may also be used.

DESCRIPTION OF CLINICAL STUDIES

Study No. 1

Fourty-six subjects, 16 women and 30 men, whose age ranged from 32–66 years, (mean age 51 years), with untreated mild essential hypertension - diastolic blood pressure between 90 and 104 mm Hg recorded on at least two consecutive occasions during the period of screening, participated in the study. All subjects knew that they had mild hypertension from previous examinations. No medical intervention had been carried out 2–3 months prior to the study. Other causes for hypertension were excluded by history, physical examination and the determination of these laboratory tests: urinealysis, serum sodium, potassium, chloride, serum creatinine, plasma renin activity (PRA), 24 hours urine for sodium, potassium and calcium—Na, K, Ca.

On each occasion throughout the study blood pressure was determined after 15 min in each position and the value recorded as a mean of these three measurements.

The mean blood pressure, MBP, used in further calculations was defined as diastolic blood pressure plus one third of puls pressure i.e. the difference between systolic and diastolic. The values used for calculation of the MBP were the averages of the three readings in each position.

The study was disigned as open placebo controlled, as is shown in FIG. 1.

In FIG. 1 the following abbrevations are used.
D=vitamin D derivative (Calcitriol(R))
PL=Placebo
R=seaweed preparation described above
R+D=seaweed preparation+vitamin D derivative (Calcitriol(R))

The study started with screening and medical examination of the patients.

Period A: 0-3 weeks of office visits with frequent blood pressure measurements, at least twice weekly, monitoring of body weight, 24-hours urine collections for Na, K, Ca during the last two days.

Period B: Fourth week—frequent blood pressure measurements, 24-hours urine collection during the last two days, being on standardized food-intake, and repeated blood samples plus cholesterol and triglycerides on the last day.

Period C: Fifth week-three days on a low sodium diet with a recommended Na content below 30 mmol/day, 24-hours urine collections during the second and third day and blood samples taken in the morning of the fourth day.

After the termination of period C all patients were divided into three groups to start treatment with R, D and R+D respectively.

Period D: 6-8 weeks—three weeks of treatment with D alone (0.5 µg/day-0.25 µg two times daily) for both groups.

Period R: Three weeks of R—treatment alone (2 g three times daily).

Period R+D: Three weeks of the combined treatment R (2 g t.i.d.) and D (0.25 µg (two times daily).

Period PL: Three weeks of the placebo treatment (capsules identical as for R two periods—wash out periods three weeks each.

All patients were asked to maintain their eating habits including salt intake and body weight throughout the study. The patients were given a written prescription for a standardized diet based in their own eating habits and were asked to observe this diet during the last three days of each treatment period before blood sampling. The standard diet contained 2450 kcal/day, 155 mmol/day of sodium and 79 mmol/day of potassium.

The patients were also given a written presciption for a low sodium diet containing less than 24 mmol/day of sodium and similar to the standard diet in amount of calories and potassium. Compliance to the diet was followed by urine Na content on the second and third days of the diet.

Patients who responded to the low sodium diet with a decrease in MBP exceeding 6.7 mm Hg (the difference necessary to obtain the power of 90% of the significance test at the 5% level) were defined and described further as the sodiumsensitive group and the remaining patients as the sodiuminsensitive group. Daily food intake for all but the last three days of the periods was ad lib.

The results are presented as the means±SD. Two tailed t-test was used for statistical comparison of differences between the groups.

Mean blood pressure during the fourth week of familiarization (period B) appeared to be significantly lower than the mean blood pressure during the first three weeks of familiarization (period A). After 3 days on a low sodium diet a further reduction of blood pressure was observed. Both R and R+D treatment caused a significant decrease of the mean blood pressure in comparison with period B. Blood pressure during R+D treatment was also significantly lower than during the vitamin D treatment alone or during the placebo and washout periods as well, FIG. 2. The two wash-out blood and washout periods as well, FIG. 2. The two wash-out blood pressure values did not differ.

The mean blood pressure lowering was significantly greater during R+D treatment than during R treatment alone. However, the mean blood pressure during both periods was significantly lower than at the start, during placebo treatment and than during both washout periods as well, FIG. 2.

Mean blood pressure decreased significantly at the end of the familiarization period (period B) and was also found significantly lowered during the period on the low sodium diet (period C, not shown).

In comparison to the placebo treatment there was no significant decrease in MBP after the treatment with D alone (period D). (FIG. 2).

Figure 2:
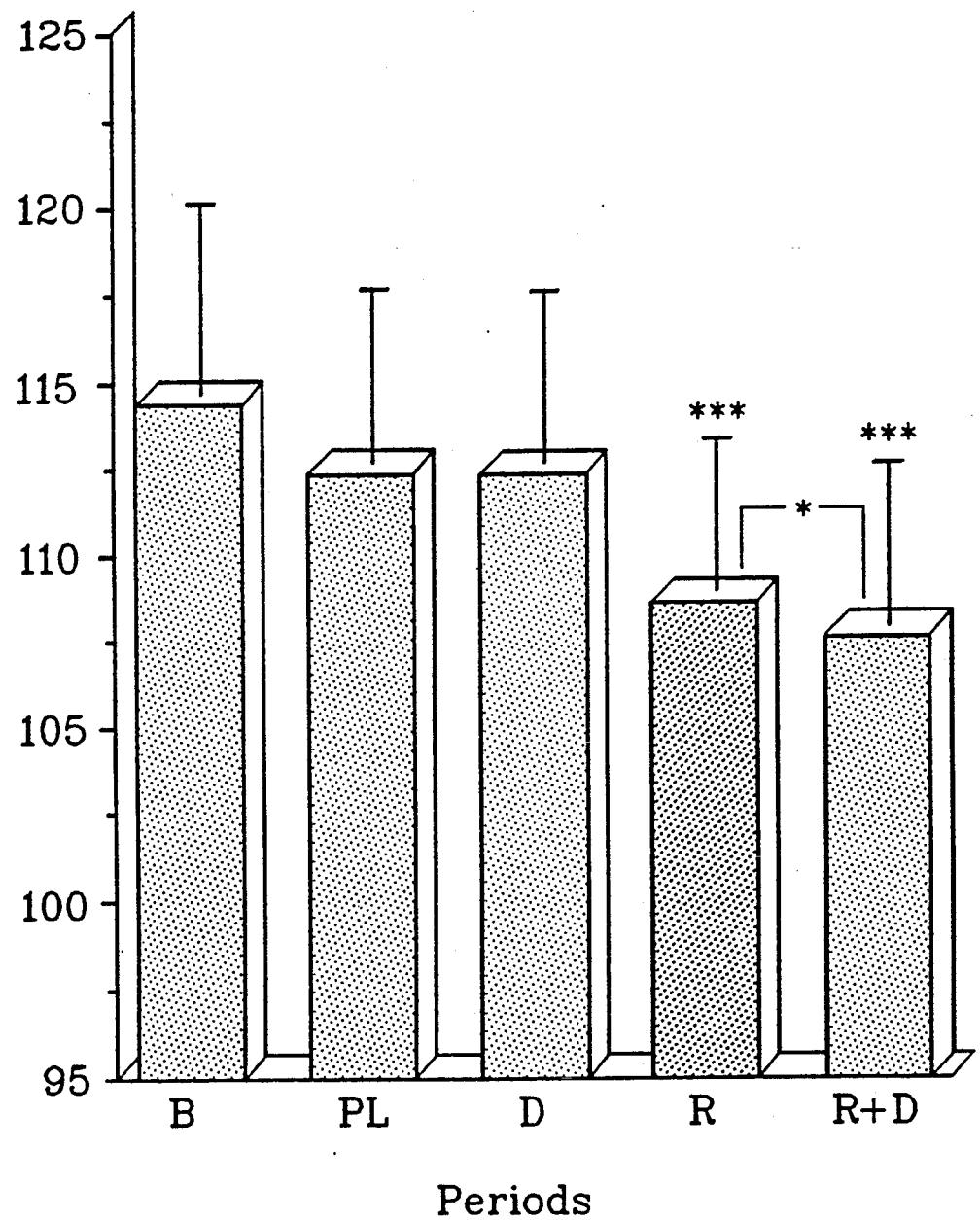
FIG. 2 is a staple diagram showing the mean blood pressure (MBP) during the comparative study.

Treatment with the seaweed preparation R alone (period R) was associated with the significantly lower MBP than that observed during the corresponding treatment with placebo (period PL) and familiarization (period B)—FIG. 2.

Figure 3:
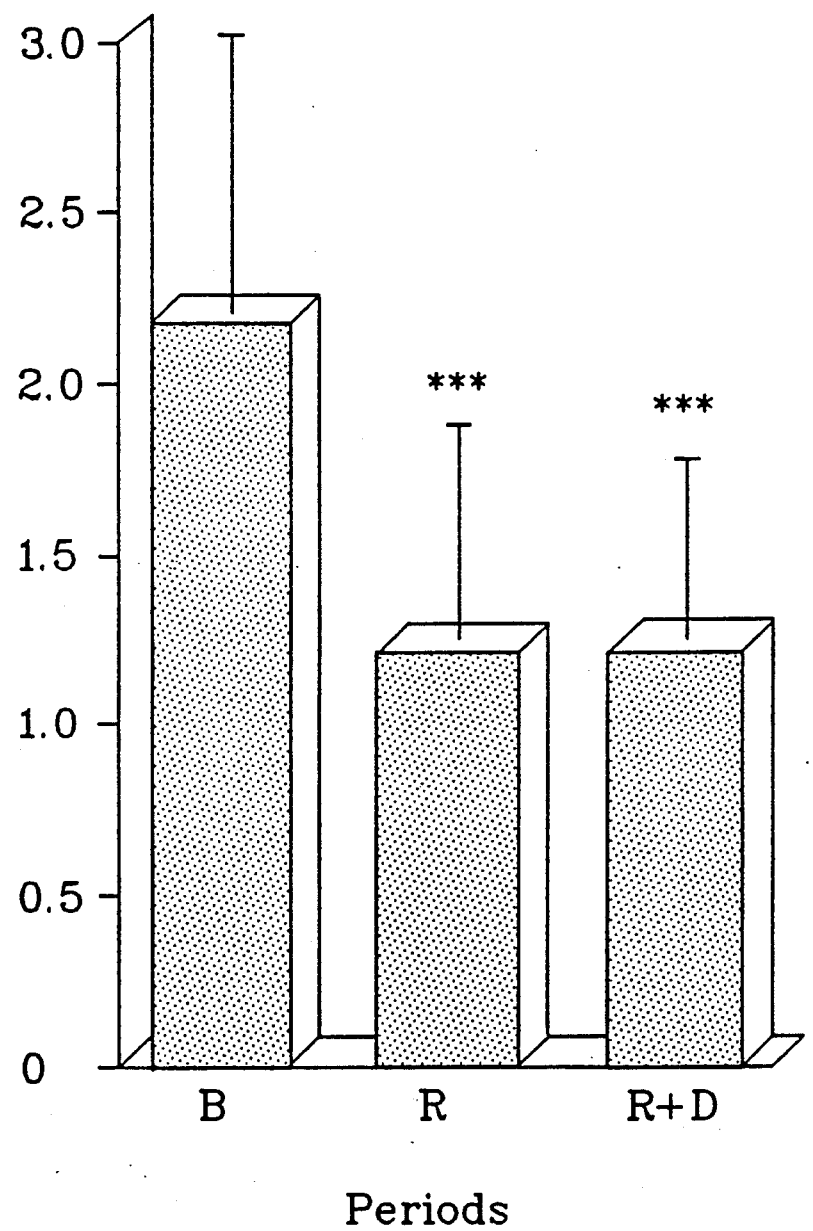
FIG. 3 is a staple diagram showing the Na/K-relation in urine during the comparative study.

The urinary sodium/potassium ratio decreased significantly during the treatment with both R and R+D (FIG. 3). No changes in the urinary sodium and potassium excretion have been observed during placebo and D treatment periods (not shown).

Urinary calcium excretion decreased significantly during the periods on the low sodium diet and during the treatment with R. The addition of D to the R administration prevented the decrease of calciuria, the excretion of calcium in urine being even significantly ($p<0.05$) higher than that observed during the familiarization period.

The decrease of MBP during different treatment periods did not differ between low and high PRA and sodium-sensitive and-insensitive groups (not shown).

The application of the vitamin D derivative alone did not cause any significant decrease of either systolic or diastolic blood pressure. While not effective alone, the vitamin D derivative evokes a synergistic effect when given together with the seaweed preparation R increasing the total decrease in mean blood pressure in the patients with mild hypertension.

The mechanism of the synergistic effect of vitamin D remains unknown, but deserves attention as this natural component potentiates the effect of the seaweed preparation without any detectable side effects. Not being sure about the possible mechanisms, the observed changes in the excretion of calcium nevertheless allow for some speculation.

Seaweed preparations have been used for binding and elimination of bivalent and heavy metals. The binding of calcium could theoretically lead to relative calcium depletion. Calcium depletion is discussed as a possible blood pressure elevating factor and could be prevented by the addition of vitamin D. Thus, theoretically, seaweeds could decrease the absorption of calcium and the supplementation with vitamin D could counteract this action.

Such an interpretation could explain the observed decrease in urinay calcium excretion on alginate treatment and the consecutive increased calciuria when on alginate with vitamin D. On the other hand low sodium intake was found to decrease the urinary excretion of calcium, to a higher extent than alginate. This could indicate that lowering of sodium intake as such is responsible for the decreased absorption of calcium.

Neither administration of R nor R+D caused any change in serum calcium concentration, indicating that possible changes in the absorption of calcium are more related to the total calcium content, intracellular calcium or total calcium turnover.

Possible effects through other quantitative or qualitative dietary changes seem unlikely, as no change in body weight has been noted throughout the study and patients remained on the standard diet during both pre- and post treatment blood pressure measurements and blood and urine sampling.

In summary the present study shows that the combination of vitamin D derivative and seaweed preparation (alginate) exerts a clear antihypertensive effect. The blood pressure lowering effect probably depends in the synergistic effect of the decreased absorption of sodium together with the increased absorption of calcium. The effect of alginate—vitamin D combination was found to be significantly stronger than of either component alone.

Study No.2

Below a further comparative study of the antihypertensive effect of the preparation according to this invention (0.02 µg vitamin D (Calcitriol(R)) and 0.5 g seaweed preparation R and a hydrochlorothiazide preparation Esidrex K will be described.

Twenty eight subjects, 10 women and 18 men participate in the study, age range from 32-60 years, mean age of 50 years, with untreated mild essential hypertension—diastolic blood pressure between 90 and 104 mm Hg recorded on at least two consecutive occasions during the period of screening. All subjects knew that they had mild hypertension from previous examination. No intervention had been 2-3 months prior to the study. Other causes for hypertension were excluded by history, physical examination and the determination of these laboratory tests:

Urinalysis, serum sodium, potassium, chloride, serum creatinine, plasma renin activity (PRA), 24 hours urine for sodium, potassium and calcium (Na,K,Ca).

The mean blood pressure (MBP) used in further calculations was defined as a diastolic blood pressure plus one third of puls pressure i.e. one third of the difference between systolic and diastolic. The values used for calculation of the MBP were the averages of the three readings in each position.

The study was designed in periods A-G described below:

Period A: 0-3 weeks frequent blood pressure measurements—at least twice weekly, monotoring of body weight, 24-hours urine collections for Na, K,Ca during the last two days.

Period B: fourth week—frequent blood pressure measurements, 24-hours urine collection during last two days being on standardised food intake and repeated blood samples plus cholesterol and triglycerides on last day.

Period C: fifth week—three days of low sodium diet with the recommended Na content bellow 30 mmol/day, 24 hours urine collections during second and third day and blood samples taken in the morning on the fourth day.

Period D: 6-8 weeks—three weeks of treatment with seaweed extract preparation R with vitamin D or Esidrex K). Blood pressure and body weight measurements twice a week, urine collections on the last two days of the period and blood sampling on the last day.

Period E: 9-10 week—two weeks of wash-out—monitoring of blood pressure and body weight.

Period F: 11-13 week—after cross-over, the same general procedure and measurements as in period D.

Period G: two weeks of wash-out—monitoring of blood pressure and body weight.

Patients have been randomly allocated into two groups receiving seaweed preparation, 6 gram/day with vitamin D, 15 min before or at the begining of every meal or Esidrex K 1 tabl/day.

All patients were asked to maintain their eating habits including salt intake and body weight throughout the study.

The patients were given written prescription of a standardized diet based on their own eating habits and were asked to observe this diet during last three days of each treatment period before blood sampling. The standard diet contained 2450 kcal/day, 155 mmols/day of sodium and 79 mmols/day of potassium. The patients were also given written prescription of low sodium diet containing less than 24 mmols/day of sodium and similar to standard diet amount of calories and potassium. Compliance of the diet was followed by urine Na content on second and third days of diet. Daily food intake for all but the last three days of the periods was ad lib.

The results are presented as the mean±SD. Two tailed t-test was used for statistical comparison of differences between groups.

Figure 4:
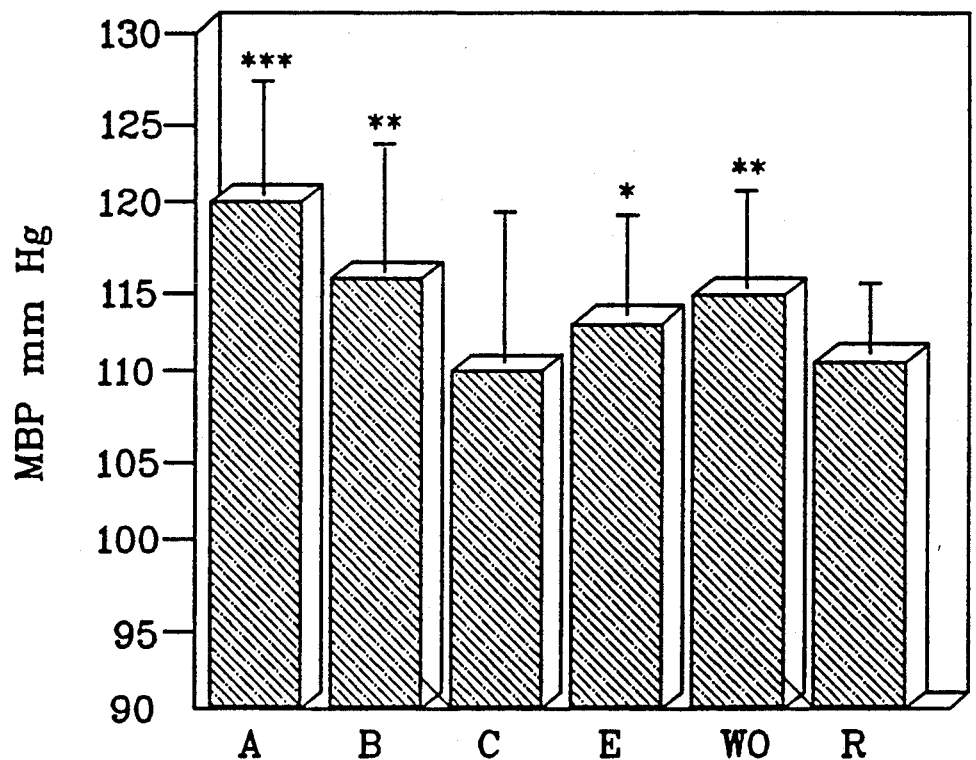
FIG. 4 is a staple diagram showing the MBP during a further comparative study of the preparation according to the present invention and a hydrochlorothiazid preparation.

The mean blood pressure (MBP) after 3 weeks of R+D treatment was significantly lower than after adequate period of Esidrex administration as well as compared with MBP in fourth week of the familiarization period. The results are shown in FIG. 4.

The upright blood pressure when measured during R+D treatment was significantly lower than during Esidrex K treatment both systolic and diastolic values. Supine blood pressure did not differ.

Figure 5:
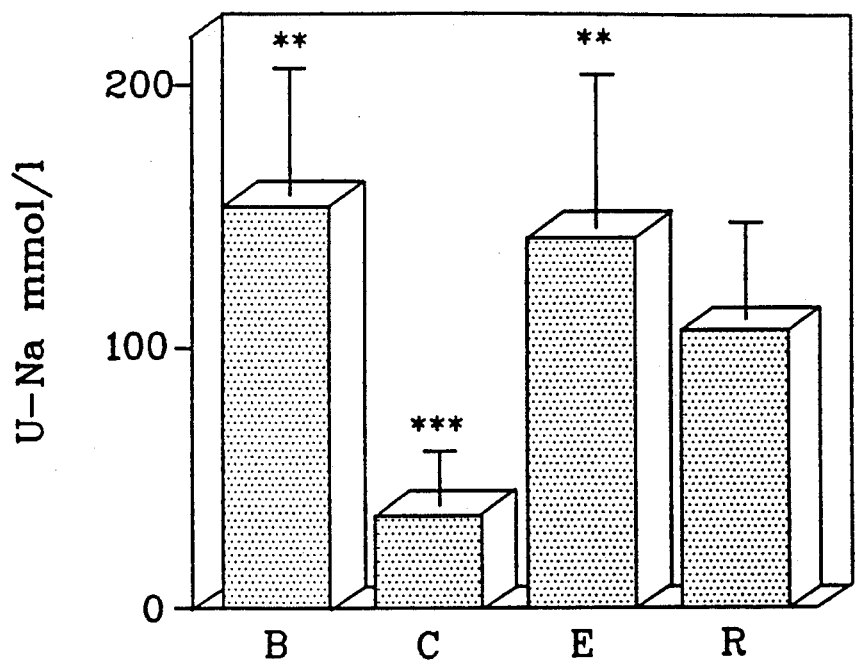
FIG. 5 is a staple diagram showing the urinary secretion of sodium during different periods of the further comparative study.

Urinary excretion of sodium was significantly lower during R+D treatment than during period B as well as during Esidrex-treatment. This is shown in FIG. 5.

Figure 6:
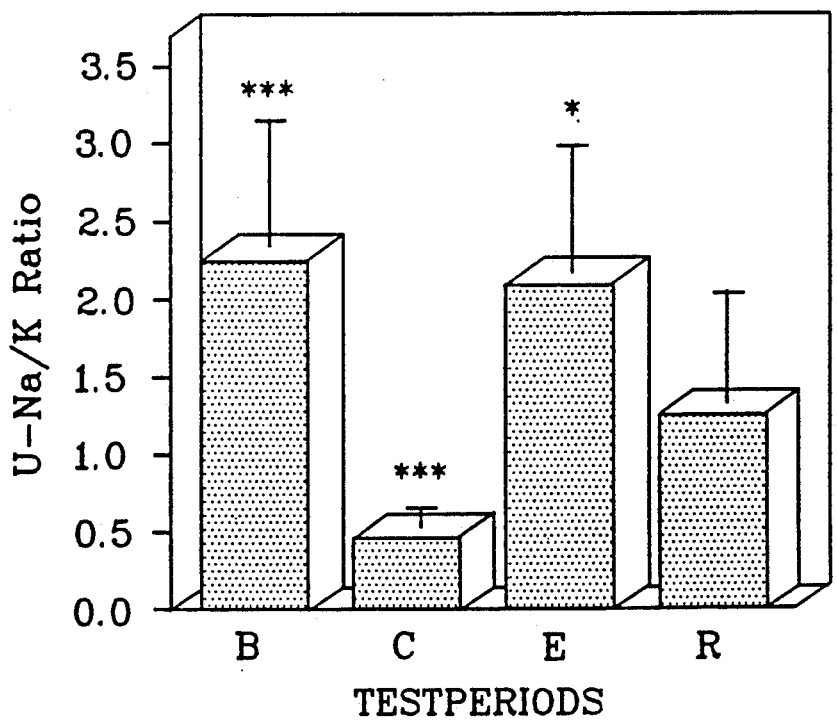
FIG. 6 is a staple diagram showing the Na/K-ratio in urine during the further study.

Urinary excretion of potassium was significantly lower, $p<0.05$, during R+D treatment than in period B although did not differ to that during Esidrex treatment. However urinary sodium/potassium ratio was significantly lower during R+D treatment than during period B and Esidrex K treatment as well, which is shown in FIG. 6.

There were no differences in plasma renin activity (PRA) during periods B, R and E. The PRA after low sodium diet rose significantly.

This study clearly shows an improved blood pressure - lowing effect for the preparation according to the present invention (seaweed preparation (alginate)+-vitamin D) as compared to Esidrex K - treatment. The preparation could therefore be recommended as an alternative or valuable aid to traditional pharmacological treatment of mild hypertension.

In the described tests potassium alginate is used as sodiumbinding polymer. It is however probable that other alginates, e.g. calcium alginate, and also other polysaccharides and other esculent polymeric substances with sodium—binding (ion-exchanging) capacity, would have a corresponding effect.

I claim:

1. A method for the treatment of hypertension in mammals comprising administering an effective amount of a composition comprising an alginate substance with sodium-binding capacity and vitamin D to said mammal in need of treatment.

2. The method of claim 1, wherein the alginate has ion exchanging properties.

3. The method of claim 1, wherein the alginate is potassium alginate.

4. The method of claim 1, wherein said alginate is present within fibers.

5. The method of claim 2, wherein said alginate is present within fibers.

6. The method of claim 3, wherein said alginate is present within fibers.

7. The method of claim 4, wherein said fibers are brown algae seaweed fibers.

8. The method of claim 5, wherein said fibers are brown algae seaweed fibers.

9. The method of claim 6, wherein said fibers are brown algae seaweed fibers.

10. The method of claim 1, wherein said alginate is prepared by acid extraction of seaweed followed by neutralizing said extract, adding a metal salt to form metal alginate, adding an acid to form alginic acid, and neutralizing said alginic acid with an alkaline potassium compound.

11. The method of claim 10, wherein said seaweed is Asophylum nodosum.

* * * * *